(12) United States Patent
Brown

(10) Patent No.: US 8,808,766 B2
(45) Date of Patent: Aug. 19, 2014

(54) HERBAL COMPOSITIONS FOR THE CONTROL OF HEMATOPHAGOUS PARASITES

(76) Inventor: Roy Walter Brown, Kirkbymoorside (GB)

( * ) Notice: Subject to any disclaimer, the term of this patent is extended or adjusted under 35 U.S.C. 154(b) by 114 days.

(21) Appl. No.: 13/147,036

(22) PCT Filed: Feb. 5, 2010

(86) PCT No.: PCT/GB2010/000216
§ 371 (c)(1),
(2), (4) Date: Jul. 29, 2011

(87) PCT Pub. No.: WO2010/089567
PCT Pub. Date: Aug. 12, 2010

(65) Prior Publication Data
US 2011/0300108 A1  Dec. 8, 2011

(30) Foreign Application Priority Data

Feb. 6, 2009 (GB) .................................. 0901918.3

(51) Int. Cl.
*A61K 36/58* (2006.01)
*A61K 36/00* (2006.01)
*A01N 65/08* (2009.01)
*A61K 36/9068* (2006.01)
*A01N 65/10* (2009.01)
*A01N 65/00* (2009.01)
*A61K 36/484* (2006.01)
*A61K 36/185* (2006.01)
*A61K 36/235* (2006.01)

(52) U.S. Cl.
CPC ............ *A01N 65/08* (2013.01); *A61K 36/9068* (2013.01); *A01N 65/10* (2013.01); *A61K 36/58* (2013.01); *A01N 65/00* (2013.01); *A61K 36/484* (2013.01); *A61K 36/185* (2013.01); *A61K 36/235* (2013.01)
USPC .......................................... 424/751; 424/725

(58) Field of Classification Search
None
See application file for complete search history.

(56) References Cited

U.S. PATENT DOCUMENTS

| 5,989,560 | A  * | 11/1999 | Terry et al. ..................... 424/736 |
| 7,179,479 | B1 * | 2/2007  | Ahn et al. ...................... 424/406 |
| 2003/0091657 | A1 * | 5/2003  | Chiasson ....................... 424/725 |
| 2003/0198659 | A1 * | 10/2003 | Hoffmann et al. ............. 424/411 |
| 2006/0148842 | A1 * | 7/2006  | Scialdone et al. ............. 514/299 |
| 2006/0216367 | A1 * | 9/2006  | Taylor et al. ................... 424/757 |
| 2007/0020304 | A1 * | 1/2007  | Tamarkin et al. ............. 424/405 |
| 2008/0113042 | A1 * | 5/2008  | Chu et al. ...................... 424/725 |
| 2008/0213590 | A1 * | 9/2008  | Greiner et al. ................. 428/401 |
| 2008/0292560 | A1 * | 11/2008 | Tamarkin et al. ............... 424/45 |
| 2009/0068255 | A1 * | 3/2009  | Yu et al. ........................ 424/450 |
| 2009/0215859 | A1 * | 8/2009  | Thummel et al. ........... 514/44 A |

FOREIGN PATENT DOCUMENTS

| CN | 101129142 | * | 2/2008 |
| GB | 2448870 | * | 5/2008 |
| WO | WO 2007/129818 | * | 11/2007 |

* cited by examiner

*Primary Examiner* — Chris R Tate
(74) *Attorney, Agent, or Firm* — Simana Rao, Esq.; William Hare, Esq.; McNeely, Hare & War LLP

(57) ABSTRACT

There is described an herbal hematophagous parasite control composition which comprises *Picraena excelsa* (Quassia), *Foeniculum vulgare* (fennel) and *Azadirachta indica* folium (Neem) provided that the composition is substantially free *Juglans nigra* folia (black walnut) and/or *Allium sativim* (garlic). There are also described a method of controlling hematophagous parasites.

17 Claims, No Drawings

HERBAL COMPOSITIONS FOR THE CONTROL OF HEMATOPHAGOUS PARASITES

CROSS-REFERENCE TO RELATED APPLICATIONS

This application claims priority to PCT International Application No. PCT/GB2010/000216 filed on Feb. 5, 2010, and published as WO 2010/089567, which claims priority from GB Patent Application No. 0901918.3, filed Feb. 6, 2009, both applications being incorporated herein in their entirety by reference.

FIELD OF THE INVENTION

The present invention relates to a novel composition for the control of hematophagous parasites, to methods of their preparation and to uses related thereto.

More particularly the invention relates to compositions for the control of ticks and similar species.

BACKGROUND TO THE INVENTION

Hematophagous parasites and the diseases they transmit are an increasing problem in animal husbandry and human health. Hematophagous parasites include ecto-parasite species, such as the tick, mite, flea, mosquito, midges, oestridae (bot flies), hypodermae (warble flies) and endo-parasite species, such as worms, e.g. liver flukes, filarial and tape worms.

In particular, infestations of hard bodied ticks (*Ixodes* in Europe and North America and *Amblyomma* and *Dermacentor* in North America) can affect a variety of animals, including, but not limited to sheep, deer, mice and red grouse. Grouse and other ground nesting birds such as Curlew, Golden Plover and Lapwings especially young birds are highly susceptible to tick burdens and tick borne diseases (TBDs). Therefore, tick infestations present a significant problem in economic, animal welfare and human health terms on moorland habitats.

Ticks often carry one or more diseases and often transmit such diseases from one host to another. It some populations around 40% of the ticks sampled carry one or more tick borne pathogens (there are 19 affecting humans, mammals and birds in Europe alone). In humans ticks may transmit a variety of diseases such as Lyme disease, Human Granulocytic Anaplasmosis and in dogs, Babesia (Red Water Fever).

The life cycle of the tick is complex. Ticks feed on a wide range of hosts. At the larval and/or nymph stage, the male or female tick larvae or nymph will feed on small mammals, rodents as well as larger hosts such as deer, sheep, companion animals and humans. In the adult stage, only the female tick will blood feed and generally will feed normally on larger animals, mammals, such as deer, hare and sheep or birds such as grouse. Once the adult female has fed, she will lay her eggs and die if she has mated. Importantly, when the female takes a blood feed the blood stream of the host passes through the tick and hence a tick borne disease may be more easily transmitted that with other hematophagous parasites, such as fleas or mosquitoes.

The problems caused by ticks are increasing. In the USA in 2007 there were 57,000 confirmed cases of Lyme Disease in humans alone and many other cases of tick borne disease (TBD). Indeed, the UK has seen its first case of tick borne encephalitis in 2008. Lyme disease, which is one of the most common tick borne diseases in humans, is classified as an emerging infectious disease (EID), that is, an infectious disease whose incidence has increased in the past 20 years and threatens to increase in the near future.

There are numerous tick killing or repelling treatments available, but none are satisfactory in that they are either considerably toxic to one or more of the species threatened by tick borne diseases. For example sheep are normally dipped in organophosphorous sheep dips. However such compounds are very toxic to humans, as they travel easily through the skin. More recently synthetic pyrethroids have replaced organophosphorous compounds, as they are much less harmful to humans. However, it is known that synthetic pyrethroids cause environmental damage to fresh water invertebrates, such as beetles, dragonflies, crayfish and the like. With both organophosphorous and synthetic pyrethroid dips, drenches and pour ons there are issues over long term efficacy and withdrawal periods before meat enters the human food chain. This is particularly important when considering 'wild meat' such as deer and grouse. There are also general concerns over long term efficacy.

It is desirable to provide a systematic remedy, since topical applications may provide efficacy for a limited period of time. However, known systemic remedies often cause vomiting in animals when administered enterally.

More recently attempts have been made to produce herbal tick remedies. For example, UK Patent Application No. 2448870 describes herbal tick remedies comprising, significant amounts of *Allium sativim* (garlic) and *Juglans nigra* folia (black walnut); as well as *Picraena excelsa* (Quassia), *Foeniculum vulgare* (fennel) and *Azadirachta indica* folium (Neem). More specifically, UK Patent Application No. 2448870 describes a herbal tick remedy consisting of a composition with the following ingredients, wherein the relative ratios are shown in brackets, *Allium sativim* (garlic)(2), *Juglans nigra* folia (black walnut)(2), *Picraena excelsa* (Quassia)(1), *Foeniculum vulgare* (fennel)(1) and *Azadirachta indica* folium (Neem)(1).

It is clear for example that in the trials exemplified in example, UK Patent Application No. 2448870 the herbal tick remedy may be effective in the brown hare, but not in red deer, where it is seen to be either ineffective or have a deleterious effect. Furthermore, later trials with these formulations have shown that efficacy is not sustained beyond 8 months.

Therefore, there remains a need for an environmentally friendly tick remedy which does not suffer from the disadvantages hereinbefore described.

SUMMARY OF THE INVENTION

We have found that the presence of too much *Juglans nigra* folia (black walnut) and/or too much *Allium sativim* (garlic) can cause liver or kidney problems in animals treated with such a remedy. Therefore an herbal composition in which *Juglans nigra* folia (black walnut) and/or much *Allium sativim* (garlic) are absent will be advantageous.

Therefore, according to a first aspect of the invention we provide an herbal hematophagous parasite control composition which comprises *Picraena excelsa* (Quassia), *Foeniculum vulgare* (fennel) and *Azadirachta indica* folium (Neem) provided that the composition is substantially free of *Juglans nigra* folia (black walnut) and/or *Allium sativim* (garlic).

In the herbal hematophagous parasite control composition of the invention it is desirable that the composition is substantially free of *Juglans nigra* folia (black walnut) and *Allium sativim* (garlic). It will be understood by the person skilled in the art that trace amounts of *Juglans nigra* folia (black walnut) or *Allium sativim* (garlic) may be present, but these should not be biologically effective amounts. Alternatively, if one of *Juglans nigra* folia (black walnut) or *Allium sativim* (garlic) is present, for example in the treatment of a particular species, the other will be absent.

The composition will generally comprise an effectively parasiticidal amount by weight of *Picraena excelsa* (Quassia), *Foeniculum vulgare* (fennel) and *Azadirachta indica* folium (Neem).

The composition of the invention may also include a suitable adjuvant, diluent or carrier. Such an adjuvant, diluent or carrier may vary depending upon, inter alia, the mode of administration, the species to be treated, etc.

It will be understood by the person skilled in the art that the amounts of *Picraena excelsa* (Quassia), *Foeniculum vulgare* (fennel) and *Azadirachta indica* folium (Neem) may vary depending, inter alia, upon the species being treated, the parasite targeted, etc., therefore the ratio of *Picraena excelsa* (Quassia), to *Foeniculum vulgare* (fennel) to *Azadirachta indica* folium (Neem) may be, for example, *Picraena excelsa* (0.5 to 1.5 parts w/w), *Foeniculum vulgare* (0.5 to 1.5 parts w/w) to *Azadirachta indica* folium (1.5 to 2.5 parts w/w).

Preferably, the ratio of *Picraena excelsa* (Quassia), to *Foeniculum vulgare* (fennel) to *Azadirachta indica* folium (Neem) may be, *Picraena excelsa* (0.75 to 1.25 parts w/w), *Foeniculum vulgare* (0.75 to 1.25 parts w/w) to *Azadirachta indica* folium (1.75 to 2.25 parts w/w) and more preferably the ratio will be about *Picraena excelsa* (1 part w/w), *Foeniculum vulgare* (1 part w/w) to *Azadirachta indica* folium (2 parts w/w).

The use of *Foeniculum vulgare* (fennel) is advantageous in that, inter alia, it acts as a narcotic and therefore subdues the hematophagous parasites. *Foeniculum vulgare* (fennel) is known to treat strongylitis in red deer.

In another aspect of the invention it may be desirable to have a small amount of *Allium sativim* (garlic) present, depending upon, inter alia, the species to be treated, but this shall be a non-toxic amount of *Allium sativim* (garlic) and shall be less than the amount of *Picraena excelsa* (Quassia) or *Foeniculum vulgare* (fennel) by weight.

Alternatively, in another aspect of the invention it may be desirable to have a small amount of *Juglans nigra* folia (black walnut) present, depending upon, inter alia, the species to be treated, but this shall be a non-toxic amount of *Juglans nigra* folia (black walnut) and shall be less than the amount of *Picraena excelsa* (Quassia) or *Foeniculum vulgare* (fennel) by weight.

When *Juglans nigra* folia (black walnut) is present, the amount may vary and the ratio of *Juglans nigra* folia (black walnut) present to *Picraena excelsa* (Quassia) may be, for example, from 0.1:1 to 0.9:1 by weight, more preferably from 0.25:1 to 0.7:1 by weight, more preferably 0.5:1 by.

The use of *Juglans nigra* folia (black walnut) is advantageous in that, inter alia, it causes an oxygen surge in the host which may last for 3 to 4 hours, depending, inter alia, upon the dose. It is known in the art that the oxygen surge causes the hematophagous parasites to detach from the host. *Juglans nigra* folia (black walnut) is also advantageous in that it may cause a flushing effect in the host, which is related to the oxygen surge hereinbefore described.

An effective parasiticidal amount will be understood by the skilled person to mean an amount which results in blood and/or tissue concentrations which are toxic by ingestion by hematophagous parasites.

A particular advantageous aspect of the present invention is that we find that *Picraena excelsa* (Quassia) has a synergistic effect when combined with *Azadirachta indica* folium (Neem).

Thus, in an alternative aspect of the present invention we provide an herbal hematophagous parasite control composition which comprises *Picraena excelsa* (Quassia) and *Azadirachta indica* folium (Neem).

According to this aspect of the invention the ratio of *Picraena excelsa* (Quassia) to *Azadirachta indica* folium (Neem) may be from 1:1 to 1:10 by weight, more preferably from 1:1 to 1:5 by weight, more preferably 1:2 by weight.

In addition to the hereinbefore described synergistic effect, *Picraena excelsa* (Quassia) is able to impact on a variety of hematophagous parasites, including ticks, but also liver flukes, insects, for example, flies, such as bot flies and/or warble flies.

Other herbal ingredients may be included in the composition of the invention. The ingredient and the amount may vary depending upon the species being treated and the parasite being targeted, etc. Thus, for example, the composition may include *Glycyrrhiza glabra* (Liquorice) e.g. from 0.1 to 1.0 parts w/w, or about 0.5 parts w/w; or the composition may include *Zingiber officinale* (Ginger) e.g. from 0.1 to 1.0 parts w/w, or about 0.5 parts w/w.

Thus, an especially preferred composition may comprise *Quassia amara* (Quassia), *Foeniculum vulgare*, (Fennel), *Azadirachta indica* (Neem), *Glycyrrhiza glabra* (Liquorice) and *Zingiber officinale* (Ginger).

According to a further aspect of the present invention we provide the use of one or more of *Picraena excelsa* (Quassia), *Foeniculum vulgare* (fennel) and *Azadirachta indica folium* (Neem) in the manufacture of an herbal hematophagous parasite control composition provided that the composition is substantially free of *Juglans nigra* folia (black walnut) and/or *Allium sativim* (garlic).

According to a yet further aspect of the present invention we provide a method of controlling hematophagous parasites which comprises administration to as host an effective parasiticidal amount of a composition which comprises *Picraena excelsa* (Quassia), *Foeniculum vulgare* (fennel) and *Azadirachta indica* folium (Neem) provided that the composition is substantially free of *Juglans nigra* folia (black walnut) and/or *Allium sativim* (garlic).

According to an alternative aspect of the invention we provide a method of controlling hematophagous parasites which comprises administration to a host an effective amount of *Picraena excelsa* (Quassia) and *Azadirachta indica* folium (Neem).

In this aspect of the invention the ratio of *Picraena excelsa* (Quassia) to *Azadirachta indica folium* (Neem) is from 1:1 to 1:10 by weight.

It will be understood by the person skilled in the art that the control of hematophagous parasites may comprise the control of one or more stages of the parasite and/or one or more genders of the parasite, i.e. male and/or female. The control may comprise the killing of the parasite in situ. In addition or alternatively the control may comprise prophylaxis of the parasite. In addition or alternatively, the method may comprise control by the composition of the invention acting as a repellent.

According to the method of the invention, the administration of the effective dose to the host animal may be carried out once or a very small number of times for a duration of activity of at least one month and which can advantageously be two or three months or even six months. In other words, a permanent combating method in an environment in which the animal is subjected to strong parasitic pressure, wherein a systemic administration is carried out at a frequency well below a daily administration, such as, for example, a monthly administration, or even less than a monthly frequency, for example quarterly or half-yearly.

Since the composition of the invention comprises an herbal remedy, the composition may be administered over prolonged periods of time. For oral administration the composition can optionally be prepared at the time of use, for example by simple mixing of a powdered, or preferably dissolved, preparation into the food of the animal.

The effective parasiticidal amount administered to an animal may vary according to, inter alia, the species being treated, and may be from 0.001 to 5 g/kg of animal weight as a daily dose, or 0.01 to 5 g/kg or 1 to 2 g/kg, e.g. 1 g/kg of animal weight, the highest doses being provided for a very sustained release in the body of the animal. Similar concentrations of tincture or soya based suspension are utilised for direct ingestion or in drinking water.

However, it will be understood by the person skilled in the art that the dose may vary depending upon the species. Thus, by way of example only, a daily dose for a dog may be about 0.5 mg/kg of animal weight, a daily dose for a pony may be about 2 g/kg of animal weight, a daily dose for a ewe may be about 5 g per ewe.

Alternatively, for dosing non-domestic herds, the dose may be calculated as a feed ratio, thus, for example for dosing red deer, e.g. in a field situation, the herbal hematophagous parasite control composition may be incorporated into a feed at a ratio of from 1:10 to 1:100 parasite control composition to feed or from 1:20 to 1:75 parasite control composition to feed from 1:30 to 1:50 parasite control composition to feed.

The method of the invention may include a pre-treatment on a lower dose than the usually administered dose. Such a pre-treatment may comprise administration of a daily dose of from 0.01 to 10 mg/kg of animal weight, or 0.1 to 10 mg/kg or 0.25 to 0.75 mg/kg, e.g. 0.5 mg/kg of animal weight.

The method of the invention may further comprise the administration of a maintenance dose, which may be a lower dose than the usually administered dose. Such a maintenance dose may comprise administration of a daily dose of from 0.001 to 5 mg/kg of animal weight, or 0.01 to 1 mg/kg or 0.05 to 0.5 mg/kg, e.g. 1 mg/kg of animal weight.

It will be understood that the effective parasiticidal amount may be administered by other routes, such as a topical or transcutaneous formulation. However, an advantage of the present invention is that since it comprises an herbal remedy, it can desirably be administered enterally.

The composition may be in any suitable form for oral administration, such as, for example, solutions or suspensions to be taken orally, emulsions, microemulsions, creams, pellets, tablets, gelatin capsules or others.

It is preferable for the excipient which forms part of the composition for oral enteral administration to allow release in the intestines. For large animals, preference is given to formulations in the form of powders. When the active compound is to be administered via an animal feedstuff, it may be intimately dispersed in the feed or used as a top dressing or in the form of pellets or liquid which may then be added to the finished feed or optionally fed separately. Alternatively, feed based individual dosage forms may be used such as a chewable treat.

As hereinbefore described, the composition of the invention may be administered in a variety of forms, for example, it may be simply admixed with an animal feedstuff. However, it is advantageous if the treatment of fowl, such as grouse, to coat the composition onto a grit, e.g. after mixing or dissolving or suspending the composition into an edible oil, which is then consumed by the birds.

In a yet further aspect of the invention the composition is incorporated into a glass, e.g. a synthetic 'grit' which then functions as a grinding agent in the bird's crop. It is of course within the scope of the present invention for one composition to be incorporated into a glass and the same or different composition may be coated onto naturally occurring grit used by keepers to feed to game birds. Although the process has yet to be fully developed at a commercial scale the experimental and trial phases have established the ability to incorporate the herbal composite products into the lattice work of silicon dioxide using a very low temperature (70° C.) and high pressure (25 bar) process. This creates a stable and uniform product which in the synthetic grit is released by the grinding action in the bird's crop and through the digestive processes in the stomach of herbivores if it is incorporated into a glass bolus.

The composition of the invention may be manufactured using conventional processes known per se using common general knowledge known in the art.

Therefore, according to this aspect of the invention we provide a process of manufacturing a composition as hereinbefore described which comprises mixing the required amounts of *Picraena excelsa* (Quassia), *Foeniculum vulgare* (fennel) and *Azadirachta indica* folium (Neem).

Therefore, according to the alternative aspect of the invention we provide a process of manufacturing a composition as hereinbefore described which comprises mixing the required amounts of *Picraena excelsa* (Quassia) and *Azadirachta indica* folium (Neem).

However, an especially advantageous aspect of the invention provides a process for the manufacture of a composition of the invention may be produced by cell culture techniques. Such a method is advantageous in that, inter alia, the composition may be produced with a predetermined ratio of components. Furthermore, this aspect of the invention may produce the active ingredients in the form of a gel or a concentrate which can readily be formulated into a feedstuff, bolus, paste or the like.

Thus, according to this aspect of the invention we provide a process of manufacturing a composition as hereinbefore described which comprises culturing cells of *Picraena excelsa* (Quassia), *Foeniculum vulgare* (fennel) and *Azadirachta indica* folium (Neem) together or separately. Cell culture is achieved by 'growing' selected cells or small sections of uniform tissue from the herbs in a controlled growth medium until a concentrated 'soup' is created. This is decanted and can be used in dried, solid form or as a liquid or paste. Total purity and predictable, consistent efficacy are guaranteed by this newly developed technology.

Alternatively, the process comprises culturing cells of *Picraena excelsa* (Quassia) and *Azadirachta indica* folium (Neem) together or separately.

A composition comprising a silica based bolus is a particularly desirable aspect of the present invention since this may comprise a slow release hematophagous parasite control composition which comprises *Picraena excelsa* (Quassia), *Foeniculum vulgare* (fennel) and *Azadirachta indica* folium (Neem); and is desirably substantially free of *Allium sativim* (garlic) and/or *Juglans nigra* folia (black walnut) which comprises culturing *Picraena excelsa* (Quassia) cells, *Foeniculum vulgare* (fennel) cells separately or together with *Azadirachta indica* folium (Neem) cells.

In another aspect of the invention we provide the use of *Foeniculum vulgare* (fennel) in the manufacture of a composition as hereinbefore described.

Alternatively, we provide the use of *Azadirachta indica* folium (Neem) in the manufacture of one or more composition as hereinbefore described.

Alternatively, we provide the use of *Picraena excelsa* (Quassia) in the manufacture of a composition as hereinbefore described.

The composition and/or method of the invention is advantageous in that, inter alia, they may be used in the control of a variety of hematophagous parasites. Such hematophagous parasites shall include, but shall not be limited to one or more ecto-parasite species, such as the tick, mite, flea, mosquito, midges, oestridae (bot flies), hypodermae (warble flies) and endo-parasite species, such as worms, e.g. liver flukes, filarial and tape worms.

The invention will now be described by way of example only

EXAMPLE 1

Hematophagous Parasite Control Composition

The following formulation was prepared:

| Quassia | *Quassia amara* | 1 part w/w |
| Fennel | *Foeniculum vulgare* | 1 part w/w |
| Neem | *Azadirachta indica* | 2 parts w/w |
| Liquorice | *Glycyrrhiza glabra* | 0.5 parts w/w |
| Ginger | *Zingiber officinale* | 0.5 parts w/w |

Intake was either as dry powder added to food or as a solution in drinking water (also trialled in capsules on human guinea pig) equivalent to 0.5 gms/kg body weight/day for five days to reach full effectiveness, thereafter 0.25 gms/kg body weight/day to maintain efficacy.

A. Tick, Biting Fly, Midge and Worm Control in Dogs

Following on from anecdotal trials with working dogs in Cyprus, where after three days on the herbal compound (with all garlic removed for safety) all tick and midge activity ceased on five dogs whereas four untreated dogs carried high tick burdens, systematic trials were organised in the UK. In February and March 2008 19 Black Labrador bitches between 1 year 10 months and 5 years 10 months were involved in trials.

In Trial 1 10 bitches were fed on dried dog food, pre-treated with the composition of Example 1, and 9 on untreated dried dog food to insure the treated group had an intake rate of 0.5 mg/kg body weight per day for three days before the trial commenced. On day three 10 questing female ticks were applied to the scruff area of each of the 19 dogs. The number of attached ticks on each dog was recorded 48 hours and again at 72 hours after initial application.

After 48 hours the mean number of feeding ticks attached to the treated group of dogs was 0.4 as opposed to 6.0 on the untreated group. This is significant at the 99.9% level with 8 df. After 72 hours the mean number of ticks attached to the treated group of dogs was 0.2 as opposed to 5.0 on the untreated group. This is significant at the 99.99% level with 8 df. The normal 'attached' period for an engorging female tick is 5 to 7 days.

This trial has been duplicated on two further occasions with different breeds and herb concentrations and the results have been consistent.

Dogs on very low level maintenance intake (0.1 mg/kg body weight/day) of the composition of Example 1 have remained tick free in high density tick habitats for over 8 months of continuous intake.

In Trial 2, which ran in parallel with Trial 1, the worm burden in the dogs was assessed in response to the herbal intake. Prior to the feeding programme outlined in 1 above, filarial worm counts in the faeces of the 19 dogs, all of which were known to be heavily infected, were carried out and the results expressed in worm densities per cc of faecal matter. The range in the 19 dogs was from 84 to 178, with a mean of 145 and a standard deviation of 19. At the three day sample point (when the dogs had been on the herbal compound for six days) the count ranged from 0 to 15 with a mean of 7.6 and a standard deviation of 4.5 in the treated dogs the range was 121 to 201 with a mean of 149 and a standard deviation of 18.5 in the untreated dogs.

These results clearly indicate the effectiveness of the herbal intake as a vermifuge, vermicide and repelling agent to external blood feeding parasites. It should be noted that the repelling effect for ticks was recorded in dogs and humans (anecdotally on cats) but on monogastrics such as deer and horse and also on ruminants such as sheep the effect is to block and disable once the ticks attach and commence a blood feed.

The dogs were all checked by general examination, organic function and serology tests. No abnormalities were detected and other than possible caution around the level of intake of one of the herbs in pregnant bitches (or any other mammal and currently under investigation) there are no long term side effects associated with the intake of correctly formulated herbal compound taken in the right quantity.

B. Tick and Midge Response to Herbal Intake in Ponies

Trial 1. Tick Response.

In May to June of 2007 five ponies, all female, were trialled with the formula of the composition of Example 1 which was presented in the form of a powder mixed with oats at a ratio of 1 to 40 to give an intake of about 2 gm/kg body weight/day. The trial period ran over 20 days and was carried out near Crieff in Scotland. The ponies were exposed to high densities of ticks by virtue of the habitat they lived in and the attached female and nymph life stages were counted initially before feeding started. The mean count was 6.8 with a standard deviation of 1.8. All five ponies were fed on the treated oats initially and by day 6 none of the ponies had any active ticks on them, although a number of desiccating and moribund ticks remained. No new ticks were picked up in this period. On day seven one pony became unwell and appeared to be scouring, which may or may not have been related to the herbal intake. This pony and two others were then fed separately on untreated oats for the remaining 6 days of the trial.

The other two ponies remained on the herbal compound. All five had access to the same tick infested area. By day eight the three ponies on untreated oats were carrying ticks again, whilst those on the herbal feed did not.

The feeding trials had to be terminated on day 12 and all ponies reverted to untreated oats. It was possible to continue the tick checks until day 20. Interestingly it was a further four days before the animals fed on the herbal oats started to pick up ticks again and day twenty before they were at a comparable level with the other group. These results suggest that a longer extends the period of latent cover. It is accepted that this is not a statistically robust trial, but it was repeated on the same group of ponies in August 2007 with an intake of 1 gm/kg body weight/day with a similar impact on ticks. No animals became unwell.

Trial 2. Midge Response.

Observations on deer and ponies suggested that midges, mosquitoes and biting flies seemed to avoid coming into contact with the skin of animal feeding on the herbal compounds. In parallel with Trial 1. the same group of ponies were fitted with 5×20 cm sticky collars to provide a measure of midge numbers making contact with the skin (high levels of midge activity were recorded in the area). The collars were changed daily but the midge numbers were recorded on days 1, 3, 6, 9 and 12 of the trial only. The numbers are summarised below.

Midge Counts from Sticky Collars

| Pony Number and Treatment | Midge Numbers | | | | |
|---|---|---|---|---|---|
| | Day 1 | Day 3 | Day 6 | Day 9 | Day 12 |
| Pony 1. On treated feed day 1 to day 6 | 78 | 12 | 2 | 22 | 67 |
| Pony 2. On treated feed day 1 to day 6 | 88 | 18 | 0 | 26 | 59 |
| Pony 3. On treated feed day 1 to day 6 | 91 | 22 | 3 | 29 | 72 |
| Pony 4. On treated feed day 1 to day 12 | 106 | 18 | 3 | 0 | 2 |
| Pony 5. On treated feed day 1 to day 12 | 82 | 14 | 2 | 2 | 0 |

Although the sample is too small to draw firm conclusions the repellent effect is clear with high numbers of midges re-establishing skin contact within six days of the herbal feed intake ceasing. These results and those which follow have important implications for controlling disease spread (e.g. Blue Tongue, Malaria, etc) to animals and humans.

Trial 3. Midge and Mosquito Response.

A group of 6 ponies in a heavily midge and mosquito infested area of the Somerset Levels were treated in the same way as the Crieff Ponies. Three ponies were fed on oats treated with the composition of Example 1 (intake rate 2 gms/kg body weight/day) and three on plain oats. The trial lasted 15 days and, as with Trial B.2 above, 5×20 cm sticky collars were attached but were only changed at three days, with counts being carried out on days 3, 6, 9, 12 and 15. Both midges and mosquitoes were collected. Due to limited resources the midges were estimated from small subsections of the collars but showed a similar trend to Crieff. The results for the mosquitoes, mainly genus *Anopheles* are summarised below.

Mosquito Counts on Sticky Collars

| Pony Number and Treatment | Mosquito Numbers per collar | | | | |
|---|---|---|---|---|---|
| | Day 3 | Day 6 | Day 9 | Day 12 | Day 15 |
| Pony 1. Herbal Fed | 8 | 0 | 0 | 0 | 0 |
| Pony 2. Herbal Fed | 14 | 1 | 0 | 0 | 0 |
| Pony 3. Herbal Fed | 12 | 1 | 1 | 0 | 0 |
| Pony 4. Plain Oats | 13 | 12 | 16 | 14 | 12 |
| Pony 5. Plain Oats | 17 | 13 | 22 | 15 | 14 |
| Pony 6. Plain Oats | 14 | 12 | 16 | 15 | 12 |

It is clear that mosquitoes are being effectively repelled by day 6 of intake at this level.

C. Fly, Midge and Mosquito Responses to Treated Red Deer Stags.

Trial 1. Enclosed Stags on Deer Farm. Deeside.

Observations on stags in a 40ha. enclosure indicated that there was an 'aura' around the backs, heads and antlers in velvet on the 20 or so beasts that had been feeding on the herbally enhanced buckets (using the composition of Example 1) for several months. This effect was observed in the 16 surviving beasts 12 months later. It was not possible to quantify the results but all of the stags, except one, which had a damaged antler and were surrounded by flies, but none seemed to be getting closer than about 5 cm to the skin. The deer were moving around and resting without the continuous ear flicking, twisting, shaking, tail flicking and general fidgeting, normally seen under these conditions. The unfortunate animal with damaged velvet was being plagued by some flies around the open wound but even these were few in number. This response indicated a repelling effect.

Trial 2. Enclosed Stags on Deer Farm. Perth Area.

The results from Trial C1 encouraged a more structured trial. 5 stags were put into an enclosure and given ad lib access to herbally treated nutrient buckets using the composition of Example 1 and 5 stags were put into an adjacent enclosure with ad lib access to non-herbally treated buckets. Trials commenced in October with the stags having access to the buckets through winter and spring. In late May the following year, as midge, fly and mosquito activity increased, sticky Velcro® strips, each 2×5 cm were literally catapulted onto the back of the neck. These were numbered and highly fluorescent. They remained sticky for about 60 minutes and then hardened and fell off. This process was undertaken once a day in the middle of the day for 15 days. 146 of a potential 150 collars were recovered. The midge, fly and mosquito burdens were counted and blocked for the two treatments. There were imperfections in the technique, but there was no other way of approaching the stags and the relatively large number of samples gives a reasonable statistical base.

Summary of Results

| Deer Treatment Group | Number of strips | Midge (x) | | Mosquito (x) | | Fly (x) | |
|---|---|---|---|---|---|---|---|
| | | Nos | SD | Nos | SD | Nos | SD |
| Plain Buckets | n = 72 | 12.9 | 1.7 | 8.4 | 1.4 | 16.9 | 2.2 |
| Herbal Buckets | n = 74 | 0.01 | 0.0 | 0.6 | 0.1 | 0.8 | 0.2 |

Whatever the weaknesses in the technique the differences in recovery of all three groups (midge, fly and mosquito) are significantly different between the two feeding programmes.

There is an almost total repellent effect on the midge populations and both mosquito and other biting fly groups are dramatically reduced in deer on the herbal supplement.

D. Midge Response to Treated, Sheared Sheep.

Trial 1.

24 recently sheared ewes were sampled to estimate midge skin contact over five days. Group 1 consisted of 12 ewes which had been fed on herbally treated nutrient buckets, using the composition of Example 1, for two months and Group 2 of 12 ewes fed on plain nutrient buckets for the same period of time. Previous trials had shown that it takes between 18 and 25 days for the herbal supplement to take effect in sheep. The rate of herbal supplement intake from the buckets equated to about 2 gms per ewe per day on average. The day after shearing, each ewe was fitted with a neck collar carrying a 5×20 cm sticky pad. This collar was changed on each of the five days giving 60 sample pads from each group.

Summary of Results

| | Mean Midge Density per collar (n = 60) | SD |
|---|---|---|
| Group 1. Sheep on herbally treated buckets (n = 12) | 0.6 | 0.02 |
| Group 2. Sheep on plain buckets (n = 12) | 78.7 | 8.56 |

There is an order of magnitude difference in the results and there is clearly a highly significant repelling effect. Once again the implications for controlling diseases such as Blue Tongue are obvious.

E. Tick Control Trials on Dunlossit Sheep.

Trial 1. 2007 to 2008.

Two groups of 15 ewes each were put into adjacent, tick infested enclosures and monitored for 10 months. One group was fed on molasses buckets with an herbal supplement comprising the composition of Example 1, the other on plain molasses buckets. The groups were clearly marked and had ad lib access to the buckets. The rate of intake from the buckets varied over the trial but the average daily herbal intake was calculated at 5 gms per ewe.

When the ewes were put in the enclosures they had just come off the hill and were heavily infested with ticks. The general level of exposure to new ticks declined through the autumn but there was always tick activity. The ewes in the treated group were 6 to 7 years old whilst the control group was 4 to 5 years old.

The initial check was carried out in October 2007, when four ewes from each group were handled to count the ticks, assess their condition and collect samples for disease testing.

Whilst the herbal supplement acts as a repellent to flies, midges and mosquitoes on sheep and deer it does not prevent ticks from attaching and starting to feed. Within a short time the feeding ticks appear to block and remain attached but unable to complete their feed. They desiccate and eventually die, breaking off and often leaving their mouth parts in the skin. Ticks in this condition are classed as 'moribund'.

Summary of Results October 2007

| | Female | Male | Nymph | Larva | Total |
|---|---|---|---|---|---|
| Control Group | | | | | |
| Total | 17 | 1 | 24 | 57 | 99 |
| Number Moribund/Damaged | 0 | 0 | 0 | 0 | 0 |
| % Moribund/Damaged | 0 | 0 | 0 | 0 | 0 |
| Herbally Treated Group | | | | | |
| Total | 8 | 2 | 21 | 0 | 42 |
| Number Moribund/Damaged | 2 | 0 | 11 | 0 | 31 |
| % Moribund/Damaged | 25 | 0 | 52 | 0 | 74 |

There was clearly a highly significant difference in both numbers and condition of the ticks between the two groups. Whilst the small sample (8 out of a possible 30 ewes) could produce biased results, e.g. the differences in the condition of the two groups could have an effect (healthy sheep in a ticky environment often carry a lower tick burden than weaker animals anyway) the results are too clear cut for this to be a full explanation.

The ticks tested for disease (obviously with the blood of their hosts inside them) from the control group indicated the presence of Flavivirus (Louping Ill), *Ehrlichia/Anaplasma* (Tick Borne Fever) and *Staphylococcus aureus* (Pyaemia, Septicaemia, localised skin infections) whilst those from the herbally fed group did not return Flavivirus. There is not thought to be any significance in these differences.

In a subsequent inspection in December 2007 all 30 ewes were checked. In total 515 feeding life stage (larva, nymph, female) ticks were counted on the Control Group and 202 on the Herbally Fed Group. In general terms the control group were obviously carrying many more ticks, including females and nymphs which had become fully engorged and then got trapped and died in the dense fleece around the neck, than the 'treated' animals. The latter were carrying some recently attached ticks and old bite marks, but no 'trapped' fully engorged specimens. This strongly suggests that few, if any, females or nymphs (probably larvae as well) successfully completed a feed.

In the May 2008 inspection 13 ewes from the herbally fed group were checked and all 15 of the control group. A large subsample of ticks was collected for disease testing.

Summary of Results from May 2008

| | Female | Male | Nymph | Larva | Total |
|---|---|---|---|---|---|
| Control Group | | | | | |
| Total | 153 | 5 | 98 | 9 | 265 |
| Number Moribund/Damaged | 71 | 0 | 30 | 2 | 103 |
| % | 46 | 0 | 31 | 22 | 39 |

-continued

|  | Female | Male | Nymph | Larva | Total |
|---|---|---|---|---|---|
| Moribund/Damaged Herbally Treated Group | | | | | |
| Total | 177 | 1 | 32 | 0 | 210 |
| Number Moribund/Damaged | 138 | 0 | 20 | 0 | 78 |
| % Moribund/Damaged | 78 | 0 | 63 | 0 | 37 |

The results are less clear cut than in the December 2007 sample. There was a higher percentage (22%) of active ticks on the Herbally Fed group than on previous checks, although there was still a significant difference to the 62% active on the Control Group. Ticks, whether active or moribund, were concentrated in the collar area of the Herbally Treated Group whereas on the Control Group they were recovered from muzzle, ears, collar, brisket, axillary and inguinal areas. There were clusters of mummified engorged female ticks in the collar area of both groups. The active ticks on the Herbally Fed Group were all recently attached and there were few active nymphs and no larvae recorded from this group.

A number of factors have been identified as significant in apparent reduced efficacy and have been addressed as part of the ongoing development process.
1. Intake of the supplementary feeding blocks became less as new spring grazing became available. This has lead to the development of the consistent delivery via a bolus rather than field feeding where sheep are on pastures.
2. Condition. The health of the animals is significant. In the Control Group 12 out of the 15 ewes had a tick burden but the 3 fittest animals were carrying no ticks at all. In the Herbally Fed Group animals in poorer nutritional condition were carrying more active ticks than those in better condition, a combination of lower intake/utilisation and activity (sheep in poorer condition tend to spend a lot more time lying in sheltered areas, often where ticks are most active). It is suspected that animals in poorer condition may have more prominent capillaries and are therefore easier to feed on.
3. Possible differences in levels of tick activity in the trial enclosures in different seasons.
4. Age differences between the two trial cohorts.
5. Possible decline in effectiveness of the herbal preparation with age (this has been investigated, found to be a significant factor and remedied).

It is perhaps significant that the Herbally Fed Group of Ewes produced 25 lambs from 14 animals and the Control Group produced 19 lambs from 15 animals despite the Herbally Fed Group being an average of 15 months older.

In terms of Tick Borne Pathogens the samples collected recorded Tick Borne Fever in ticks from 6 ewes in the control group and 8 ewes in the herbally fed group; Non specific *Ricketsia* bacteria in ticks from 4 sheep in the control and 3 sheep in the herbally fed group; *Staphylococcus aureus* in all 12 ewes carrying ticks in the control group and on 10 out of the 13 ewes sampled in the herbally fed group.

Despite the greater variation the fact that the number of inactive/moribund ticks on the Herbally Fed Group is twice that of the Control Group indicates the application is still highly effective.

F. Herbal Control of Ticks on Red Deer in a Field Situation.

One of the main reasons for developing the herbal compounds is to provide an effective control against ticks (and other parasites) which can be used in wild hosts and target species such as deer, mountain hares and game birds such as red grouse, pheasants and partridges as well as farm animals, companion animals and potentially humans. Conventional tick treatments have implications in terms of 'wild meat status', withdrawal periods and possible damage to aquatic ecosystems and these issues, along with several welfare concerns, have been shown to be greatly reduced by taking the herbal route, which is based on sound ethnobotanical data as well as modern assay and production.

1. Deer Trials on Islay. Following on from initial trials on enclosed red deer stags and hinds between November 2006 and April 2007 when a different formulation was used subsequent work with the current formulation was carried out on the hill. Deer in the trial areas had unrestricted access to herbally treated nutrient buckets in one area and plain buckets in another. The herbal buckets contained a ratio of 1:40 herbs to feed. Levels of tick activity were assessed by blanket dragging. Deer were culled in pairs, one from each treatment, at regular intervals and the ticks counted off with subsamples sent for pathogen testing. The deer carcasses were also inspected for other parasite activity such as Warble and Bot Fly and Liver Fluke. The results are blocked and discussed with those from the Braemar trials below.

2. Deer Trials at Braemar.

Between June and early August 2007 similar trials to the Islay programme were carried out on estates in the area to evaluate the intake of supplementary feed at a time of year when other food is widely available and to start to establish how effective short and long term exposure to the herbal feed are in terms of controlling tick activity over the summer months (winter effectiveness is established from earlier trials). As with the Islay trials deer (stags) were culled in pairs and taken to larders for examination. Ticks were counted off by life stage i.e. larva, nymph, female, male and condition i.e. active, attached/feeding, attached/moribund, dead. All areas of the underside and head areas of the stags were examined. The external condition, gut contents and condition of internal organs was assessed. Samples of dead, moribund and active ticks were collected for further analysis including evidence of viral or bacterial pathogens in the gut/host blood.

Of the 16 pairs of deer sampled in this phase tick numbers ranged from 1700 on a Control stag at Braemar down to 11 on an Herbally Fed stag at Braemar. The range in active ticks was between 84 and 99% on the Control deer from both trials and 11 to 34% on the Herbally Fed Groups. One exception to this range was a stag which was known to make excessive use of the feeding buckets. This animal was carrying very few ticks and half of those were recently attached and active suggesting that saturation with the herbal feed produces a repelling effect even in deer.

The results show a reduction in tick activity of between 70 and 80% on the Herbally Fed deer which is encouraging and there is a high degree of effectiveness even with short term, irregular low levels of herbal intake (equivalent of 0.5 gm/kg body weight/day for three days).

Ticks sampled for pathogens from both areas returned a wide range of potential Tick Borne Diseases. 162 ticks were sampled at Braemar and of these 74 were carrying one or more pathogen (45% of the sample) with 8 (5% of the sample) carrying three or more pathogens. 962 ticks were sampled from the deer on Islay. Of these 407 (42% of the sample) were carrying one or more pathogens and 84 (8.7% of the sample) were carrying three or more. Red Water Fever *Babesia divergens*, Lyme Disease group *Borrelia* spp, Louping Ill Flavivirus spp, Septicaemia *Pasturella* spp, Tick Borne Fever *Ehrlichia/Anaplasma* spp and Pyamia/skin infection *Staphylococcus aureus* were identified from feeding ticks at both Braemar and Islay with a non specific 'Spotty' Fever *Ricketsia* spp being identified from Braemar as well.

The existence of this wide range of pathogens is cause for concern, especially with the Tick Borne Fever which has an immune system depressing effect and this is likely to be having a major impact on other susceptible species, e.g., red grouse. The deer themselves are only affected to a limited extent.

The impact of the herbal compounds on worm burdens and other ectoparasites is currently being evaluated and will be reported at a later date. Initial data indicates a substantial reduction in the presence of Botfly larvae in the carcases of herbally fed deer.

The results so far confirm that herbally fed deer should be used to control tick populations rather than being culled as major hosts for ticks. Far from increasing pressure on other disease susceptible species, such as red grouse, herbally fed deer appear to reduce overall levels of tick activity and curtail the tick life cycle by preventing females from completing their final blood feed and therefore stopping egg production.

G. Herbal Control of Ticks in Farmed Red Deer Calves

Trial 1. Glen Muick, Ballatar.

Between October 2007 and September 2008 a group of 10 2007 calves were kept in enclosures in two groups. One group of five was fed on the standard ratio of herbal compound, using the composition of Example 1, mixed with coarse oats, the other group of five on plain coarse oats. In this trial it was possible to handle the animals directly in a crush area so that tick burdens could be counted and sub sampled for disease on a regular basis as well as the animals being weighed and generally assessed. The objectives of the trials were:

1. To monitor differences in general condition of the calves and the levels of tick activity in the two groups over a period of time.
2. To assess the response and condition of deliberately introduced clean (disease free) ticks on both groups over the winter period.
3. To quantify the attachment and feeding rate of wild questing ticks as the spring and autumn 'tick rises' took place.
4. To confirm the mode of action of the herbs by forensic examination of ticks collected from the calves.
5. To identify the residual effects of the herbs on the calves and the venison they produced on culling in vivo and in vitro. This was to include meat eating quality and palatability.
6. To adjust levels of herb intake as the calves grew and to monitor levels of 'background' tick activity to establish maximum efficacy with most economic use of resources, basically to fine tune levels of intake. Due to issues with quality and efficacy of one batch of the herbal mix some of these objectives could not be achieved and the trial is currently being repeated. However, significant positive results have been obtained.

In the tick application trials 44% of the female ticks applied to the control group were found to be attached and feeding 48 hours after application. On the Herbally fed group none of the applied females were attached and feeding.

The April 'wild tick' counts are summarised below and although there were concerns over the quality and rate of intake of the herb mix the figures show there is a clear response in that a large proportion of the ticks on the herbally fed deer are moribund.

Summary of Tick Activity on Trial Calves April 2008

|  | Control Group (n = 5) | Herbally Fed Group (n = 4)* |
|---|---|---|
| Females attached/feeding | 304 | 29 |
| Moribund Males | 0 | 167 |
| Males total | 117 | 17 |
| Males of which attached to females | 103 | 7 |
| Nymphs | | |
| Nymphs attached/feeding | 103 | 0 |
| Moribund Totals | 0 | 77 |
| active/attached | 524 | 46 |
| Moribund | 0 | 244 |
| overall totals | 524 | 290 |
| % moribund | 0 | 84 |

The other significant finding is that there were many more males collected from the control group and the majority of these were attached to healthy, feeding females. On the herbally feed group there were few males and less than half of these were attached to females.

The 'wild' female and nymph ticks collected for disease sampling had carried in a range of pathogens. Female ticks collected from 4 control and 5 herbal fed calves returned *Staphylococcus aureus*, 2 control and 1 herbal fed returned Tick Borne Fever, 3 control and 4 herbally fed returned a non specific *Ricketsia* and 1 control and 1 herbally fed returned Red Water Fever. This clearly indicates the potentially morbid pathology of the tick population and confirms transmission to deer hosts.

In overall summary the January counts found 100% of attached ticks on the Control Group healthy with 90% of the ticks on the Herbally Fed Calves moribund. In the April Control samples there were 43 attached feeding females (22 applied) of nymph ticks with 1 dead engorged female, giving an activity rate of 98%. In the April Herbally fed group there was 1 recently attached actively feeding female with 39 moribund females or nymphs, giving an overall activity rate of 3%. In the June samples there was 100% activity on the Control Group but 84% were moribund in the Herbally fed group. Results from September were compromised by severely by a substandard herbal feed (due to a mixing/production error there was less than 5% of the active herbal ingredients in the feed the calves had been on for the previous 8 weeks and the effectiveness had dropped by over 80%) and the results are not included here. However, the whole cycle is currently being completed.

H. Herbally Treated Grit to Control Ticks and Strongyle Worm in Grouse.

Early in the development process (October-December 2006) trials with conventional grouse grit coated with the herbal compound, using the composition of Example 1, and solutions in drinking water produced encouraging results, but uptake and longevity in hostile moorland environments proved a problem. There were also potential toxicity issues with the formulation. The effective concentration in liquid was 40 ml of tincture concentrate in 1 liter of water, coating on the grit was at the standard mix rate for this particular formulation was 25 kg powder herbal composition to 1000 kg carrier.

Throughout 2008 a novel method of producing synthetic grit under high pressure and at low temperature (70° C., one of the key active ingredients in the herbs denatures above 80° C.) in which the herbal mixtures are actually incorporated has been developed. Only one trial on 10 semi captive grouse in two groups has been carried out. One group of 5 had access to herbally treated synthetic grit and the other group of 5 to plain synthetic grit. Results are encouraging.

Summary of Synthetic Herbal Grit Trials

|  | Herbal Synthetic Grit | Plain Synthetic Grit |
|---|---|---|
|  | Caecal Dropping Strongyle Worm Count | |
| Day 1. Prior to exposure to grits. | 7500 | 7600 |
| Day 3. | 5400 | 7500 |
| Day 5. | 2600 | 7700 |
| Day 7. | 1200 | 7200 |
| Day 9. | <500 | 7400 |
|  | Tick Burden (10 Questing Nymphs applied = 50 per group) | |
| Day 1. Prior to exposure to grits. | 0 | 0 |
| Day 3. | 2 | 39 |
| Day 5. | 0 | 22 |
| Day 7. | 0 | 1 |
| Day 9. | 0 | 0 |

The results indicate a major reduction in worm burden in the herbally fed group and 80% of the applied ticks probably staying on long enough to complete a blood feed (4 to 5 days) on the control group, but only 4% of ticks attaching and apparently not staying on to complete a blood feed in the herbally treated group. Clearly more comprehensive trials are needed, especially in a field situation, but these initial results are very encouraging.

The invention claimed is:

1. An herbal hematophagous parasite control composition which comprises effective amounts of *Picrasma excelsa* (Quassia), *Foeniculum vulgare* (fennel) and *Azadirachta indica* folium (Neem leaf), provided that the composition is substantially free of *Juglans nigra* folium (black walnut leaf) and/or *Allium sativum* (garlic).

2. The herbal hematophagous parasite control composition according to claim 1, wherein the composition is substantially free of *Juglans nigra* folium (black walnut leaf) and *Allium sativum* (garlic).

3. The herbal hematophagous parasite control composition according to claim 1, wherein the composition comprises parasiticidally-effective amounts by weight of said *Picrasma excelsa* (Quassia), *Foeniculum vulgare* (fennel) and *Azadirachta indica* folium (Neem leaf).

4. The herbal hematophagous parasite control composition according to claim 1, wherein the ratio of *Picrasma excelsa* (Quassia) to *Foeniculum vulgare* (fennel) to *Azadirachta indica* folium (Neem leaf) is 0.5 to 1.5 parts w/w to 0.5 to 1.5 parts w/w to 1.5 to 2.5 parts w/w, respectively.

5. The herbal hematophagous parasite control composition according claim 1, wherein said *Allium sativum* (garlic) is present in a trace amount that is non-toxic to animals.

6. The herbal hematophagous parasite control composition according to claim 1, wherein said *Juglans nigra* folium (black walnut leaf) is present in a trace amount that is non-toxic to animals.

7. The herbal hematophagous parasite control composition according to claim 1, wherein the ratio of said *Picrasma excelsa* (Quassia) to said *Azadirachta indica* folium (Neem leaf) is from 1:1 to 1:10, by weight.

8. The herbal hematophagous parasite control composition according to claim 1, wherein the composition includes an edible oil.

9. The herbal hematophagous parasite control composition according to claim 1, wherein the composition comprises a glass.

10. The herbal hematophagous parasite control composition according to claim 1, wherein the composition further comprises *Glycyrrhiza glabra* (Liquorice) and *Zingiber officinale* (Ginger).

11. The herbal hematophagous parasite control composition according to claim 1, wherein the composition is in the form of a slow release composition.

12. An herbal hematophagous parasite control composition which comprises effective amounts of *Picrasma excelsa* (Quassia), *Foeniculum vulgare* (fennel) and *Azadirachta indica* folium (Neem leaf), provided that the composition is substantially free of *Juglans nigra* folium (black walnut leaf) and/or *Allium sativum* (garlic), wherein if an amount of *Juglans nigra* folium (black walnut leaf) and/or *Allium sativum* (garlic) is present, it is present in a trace amount that is non-toxic to animals and is less than either amount of said *Picrasma excelsa* (Quassia) or *Foeniculum vulgare* (fennel) individually.

13. A method of controlling hematophagous parasites in a host in need thereof which comprises administering to the host a parasiticidally-effective amount of the composition according to claim 1.

14. The method according to claim 13, wherein the composition administered within a feedstuff.

15. The method according to claim 13, wherein the ratio of said *Picrasma excelsa* (Quassia) to said *Azadirachta indica* folium (Neem leaf) is from 1:1 to 1:10, by weight.

16. The method according to claim 13 wherein the amount administered is from 0.001 to 0.5 g/kg of the host's weight.

17. A process for manufacturing the herbal hematophagous parasite control composition according to claim 1 which comprises combining an effective amount of *Picrasma excelsa* (Quassia), *Foeniculum vulgare* (fennel) and *Azadirachta indica* folium (Neem leaf).

* * * * *